United States Patent [19]
Horan

[11] Patent Number: 6,149,952
[45] Date of Patent: Nov. 21, 2000

[54] METHOD FOR DETERMINING DELETERIOUS BACTERIAL GROWTH IN PACKAGED FOOD UTILIZING HYDROPHILIC POLYMERS

[75] Inventor: Thomas J. Horan, Los Alamitos, Calif.

[73] Assignees: Herbert W. Stoltenberg; Ruben Stoltenberg; Edwin Laird; Thomas J. Horan Family Trust, all of, Calif.

[ * ] Notice: This patent is subject to a terminal disclaimer.

[21] Appl. No.: 09/079,797

[22] Filed: May 15, 1998

[51] Int. Cl.$^7$ .................................................... A22C 17/10
[52] U.S. Cl. ............................ 426/87; 426/383; 426/415
[58] Field of Search ............................... 426/87, 383, 415

[56] References Cited

U.S. PATENT DOCUMENTS

| 5,407,829 | 4/1995 | Wolfbeis et al. | 426/87 |
| 5,753,285 | 5/1998 | Horan | 426/87 |
| 5,916,585 | 6/1999 | Cook et al. | 424/426 |
| 5,922,281 | 7/1999 | Elgas et al. | 422/45 |

*Primary Examiner*—Gabrielle Brouillette
*Attorney, Agent, or Firm*—R. Neil Sudol; Henry D. Coleman; William J. Sapone

[57] ABSTRACT

The present invention relates to a method for determining the presence or absence of contaminating bacteria in a packaged food sample comprising storing food in a package having as a lining a hydrophilic polymeric composition, said composition preferably being permeable to water and at least one gas dissolved in water or water vapor and being selected from the group consisting of carbon dioxide, carbon monoxide, hydrogen sulfide, sulfur dioxide, hydrogen and ammonia gas and containing an indicator for detecting the presence or absence of said gas; said indicator being polymerized or dispersed throughout said polymeric composition or coated onto a hydrophobic polymeric composition.

20 Claims, No Drawings

METHOD FOR DETERMINING DELETERIOUS BACTERIAL GROWTH IN PACKAGED FOOD UTILIZING HYDROPHILIC POLYMERS

FIELD OF THE INVENTION

This invention relates to methods for detecting the existence of harmful levels of bacterial growth in packaged foods.

BACKGROUND OF THE INVENTION

The presence of undesirable bacteria, for example, Botulism sp., among others, in food products intended for human consumption has recently caused increased concern among food product manufacturers. This is due to the potential that contaminated food has for serious illness or even death as a consequence of its ingestion by the consumer. While it would be desirable to monitor contamination in every sample of food, in most cases, it is simply not possible to detect the presence of contaminating bacteria by visual or mechanical inspection. Consequently, chemical means must be used to facilitate such detection.

Although food is generally inspected prior to its being packaged, it is presently not practical to inspect each package of food for contamination individually. With increasing reglarity, outbreaks of bacterial contamination place the food-consuming public at risk.

OBJECTS OF THE INVENTION

It is an object of the invention to provide a method for detecting the presence of contaminating bacteria in a food sample, especially a food sample which has been stored in cans or other packages.

It is also an object of the present invention to provide food storage cans which have been adapted to detect the presence of contaminating bacteria in food.

It is also an object of the present invention to provide hydrophilic polymeric compositions which can be incorporated onto the lining of a food can and used to detect contaminating bacteria.

These and other objects of the present invention may be readily gleaned from the description of the invention which follows.

SUMMARY OF THE INVENTION

The present invention relates to a method for determining the presence or absence of contaminating bacteria in a package food sample comprising storing food in a package having as a lining a hydrophilic polymeric composition, said composition being hydrophilic and permeable to water, water vapor and at least one gas which is produced by a contaminating bacteria, said gas preferably being selected from the group consisting of carbon dioxide, carbon monoxide, hydrogen sulfide, sulfur dioxide, hydrogen and ammonia gas and containing an indicator for detecting the presence or absence of said gas; said indicator being polymerized or dispersed throughout said polymeric composition.

Alternatively, the indicator may be coated onto a first non-hydrophilic layer, which is then further coated with at least one additional layer of hydrophilic polymer which helps the indicator to adhere to the first layer either in combination with the permeable polymer or underneath the permeable polymer. In alternative embodiments, the polymeric composition is a laminate, comprising a first layer which further comprises at least one hydrophobic, non-permeable layer (preferably, a hydrophobic non-permeable polymeric material) which prevents the water, water vapor and/or gases to be analyzed from escaping and a second hydrophilic, permeable material which coats the first layer and within which layer an indicator is dispersed or polymerized for detecting the presence of a gas dissolved in a liquid as is generally described above. In this aspect of the present invention, an indicator may coat the first layer directly and the hydrophilic polymeric composition of the second layer is coated onto the first layer and indicator. In this aspect of the present invention, the general approach to producing a laminate is easily recognized and very wellknown by those of ordinary skill in the art. One of ordinary skill may readily modify the teachings of the present specication to produce laminates comprised of numerous layers which will fall within the scope of the present invention.

The present invention also relates to novel food cans and other packages (including flexible wrapped packages of food, such as those which are used to package, meats, fish and poultry in supermarkets and the like) which have been lined (preferably, partially) with hydrophilic polymeric compositions containing an indicator which has been polymerized or dispersed throughout the hydrophilic, permeable material or coated onto a first hydrophobic, non-permable polymeric composition(s) which is then coated with a hydrophilic, permeable composition, the food cans and other packages being capable of storing food and detecting the presence of gas released by contaminating bacteria present in the food which is stored in the cans and other packages.

The present invention is useful for detecting bacterial contamination in food which has been stored after canning or packaging for extended periods of time. Although virtually any microorganism which produces a gas during growth and/or metabolism may be detected by the present invention, particularly important microorganisms which may be detected by the present invention include bacteria such as Salmonella sp., Streptococcus sp. Shigella sp., Botulism sp., *Escherichia coli* and Coliform bacteria. A number of types of *E. coli* may be detected by the instant invention including enterotoxigenic (ETEC), enteroinvasive (EIEC), enterohemorrhagic (EHEC), enteropathogenic (EPEC) and enteradherent (EAEC), among others.

Numerous hydrophilic polymeric compositions for lining the food storage package may be used, with preferred compositions including polymeric compositions which are sufficiently permeable to water, water vapor and to gas produced by contaminating bacteria to allow diffusion of the gas indicative of contamination through the hydrophilic composition to a reactive site on an indicator dispersed or polymerized throughout the composition or coated directly onto the can liner (which is further coated with a hydrophilic polymeric composition) without allowing the food stored within the package to leak or come into contact with a package lining to be avoided, such as the steel lining of a food can. In preferred embodiments according to this aspect of the present invention, the lining of the can may be coated with a hydrophobic material, preferably a non-permeable hydrophobic material which substantially will prevent water and/or gas from diffusing out of a second layer which coats the first layer comprising a permeable, hydrophilic polymeric composition and reacting or otherwise affecting the material from which the can is made.

Indicators include those which are well known in the art. The indicators which find preferred use in the present invention are those which provide a calorimetric reaction upon exposure to the gases produced by contaminating microorganisms. Gases which are produced by contaminating microorganisms include, for example, carbon dioxide, carbon monoxide, hydrogen sulfide, hydrogen, sulfur dioxide and ammonia. Certain of these gases in water produces an acid (carbonic, sulfuric) or a base (ammonia) which reacts with the chosen indicator to produce a calorimetric reaction, thus indicating the presence or absence (in the case where no reaction occurs) of contaminating bacteria. Other of these gasses, e.g., hydrogen and carbon monoxide, is itself a reactive species which reacts directly with the indicator producing a calorimetric reaction.

DETAILED DESCRIPTION OF THE INVENTION

The following terms will be used throughout the specification to describe the present invention.

The term "hydrophilic, permeable polymeric composition" is used to describe the chemical lining of the food storage containers or plastic wrap according to the present invention which contains indicator, whether polymerized or dispersed within the composition or coated onto the composition. Hydrophilic, permeable polymeric compositions include those which have a permeability to water and/or water vapor (which water or water vapor includes dissolved gasses) sufficient for allowing the water and water vapor (including the dissolved gasses) to readily diffuse through. Preferably, the hydrophilic polymeric compositions according to the present invention are also separately permeable to gasses including carbon dioxide, carbon monoxide, hydrogen sulfide, hydrogen, sulfur dioxide and ammonia, among others, such that the concentration of gas which may ultimately diffuse through the polymeric composition is sufficient to produce a visual calorimetric reaction with indicators which are included within the hydrophilic polymeric compositions. Polymers having permeabilities to water, water vapor and any one or more of carbon dioxide, carbon monoxide, hydrogen sulfide, hydrogen, sulfur dioxide and ammonia are particularly preferred for use in the present invention.

Polymeric compositions for use in the present invention include polymers which are comprised of substantial quantities of monomers having polar groups associated with them, such that the overall polymeric composition is rendered hydrophilic. Preferably, the polymeric compositions are comprised of monomers which contain for example, hydroxyl groups, ester groups, amide groups, urethane groups or carboxylate (ionized carboxylic acid) groups (such as are available from, for example, methacrylic acid). While not being limited by way of theory, it is believed that the inclusion of polar groups allows water to more readily permeate the polymer and consequently, bring dissolved gasses into proximity of the indicator for reaction. A number of hydrophilic, permeable polymers may be used in the present invention and include, for example, (poly) hydroxyethyl methacrylate, (poly)hydroxypropyl methacrylate, (poly)glycerol methacrylate, copolymers of hydroxyethyl methacrylate, hydroxypropyl methacrylate or glycerol methacrylate and methacrylic acid, aminoacrylate and aminomethacrylate, (poly)vinyl pyrrolidone, (poly) vinylpyridine, polar nylons and other polyamides, among others, including, for example, cellulosics, such methyl cellulose, copolymers of these cellulose monomers, hydroxypropyl cellulose, hydroxyethyl cellulose, hydroxypropyl methylcellulose, ethyl hydroxyethylcellulose, carboxymethyl cellulose, cellulose acetate, cellulose acetate butyrate, cellulose acetate propionate, cellulose nitrate, among others, including for example, polytetrafluoroethylene, polytetrafluoroethylene/hexafluoropropene copolymers, polyvinylphenylketone, vinylene carbonate, isopropenyl acetate, vinylbutylether, polyesters or polyurethanes containing a high percentage (at least about 10% by weight, preferably at least about 25% by weight or more) of polyethylene oxide, vinyl formate, among numerous others, including hydrophilic copolymers or mixtures of hydrophilic monomers. Additional copolymers which may be used in the present invention include those which contain at least a substantial amount of at least one or more of the above-mentioned hydrophilic monomers, including, for example, styrene/methacrylic acid/hydroxyethyl methacrylate copolymers, styrene/methacrylic acid/hydroxypropyl methacrylate copolymers, methylmethacrylate/methacrylic acid copolymers, ethyl methacrylate/styrene/methacrylic acid copolymers and ethyl methacrylate/methyl methacrylate/ styrene/methacrylic acid copolymers, copolymers based upon the cellulosics, copolymers which utilize vinylpyrrolidone monomers, among numerous others.

Other polymers which may be used in the present invention include those which are typically used to line cans or make food wrap, for example, polyvinyl acetate, polyvinyl alcohol and copolymers of polyvinyl alcohol and polyvinylacetate, polyvinylchloride copolymers of polyvinylacetate and polyvinylchloride and hydroxyl-modified vinyl chloride/vinyl acetate copolymers (for example, vinyl VAGH and VyHH copolymers available from Union Carbide). Additional, preferred polymers include those which are permeable to one or more of carbon dioxide, carbon monoxide, hydrogen sulfide, hydrogen, sulfur dioxide or ammonia gas produced by the contaminating bacteria. Additional exemplary polymeric compositions for use in the present invention include for example, low and medium density polyethylene, ethylene vinyl acetate copolymer, various polyamides including, for example, poly(imino(1-oxohexamethylene) (Nylon 6), among others, various polyesters including poly(ethylene terephthalate), polyesters containing polyethylene or polyethylene glycol block copolymers, polyurethanes containing polyglycerine or polyethylene glycol block copolymers. All of these polymeric compositions may be used because they are permeable to water, water vapor and at least one of carbon dioxide, carbon monoxide, hydrogen sulfide, sulfur dioxide, hydrogen and ammonia. Mixtures of these compositions may also be used in order to obtain polymers which have desired attributes of hydrophilicity and permeability and have sufficient structural integrity to be useful as can linings and in food storage applications, such as barrier coatings and food wrap. One of ordinary skill in the art readily will be able to modify the polymeric composition in order to facilitate its use in the present invention, depending upon, for example, the type of microorganism (and the metabolic gas) to be detected in the stored food.

The polymeric compositions according to the present invention are hydrophilic in order to allow water within which gasses are dissolved to permeate throughout the polymeric composition, thus providing a means to deliver gasses or other reactive species (in certain cases, produced from an interaction of the water and the gas, such as the production of carbonic acid from carbon dioxide and water) to the indicators which are dispersed or polymerized throughout the polymeric composition. The result is a calorimetric reaction which clearly evidences the existence of gasses which are produced by contaminating bacteria or other microbes. This approach also maximizes the likelihood that water or water vapor associated with the stored food will come into contact with indicator, thus maximizing the possibility of a reaction between a dissolved gas (or a reactant produced from such gas) with the indicator. Without being limited by way of theory, it is believed that the ability of the gas-containing liquid in the food sample to permeate the hydrophilic resin and maximize the possibility of a reaction between a dissolved gas (or reactant produced from such gas) and indicator to produce a visual (calorimetric) reaction. In this way, the present invention is superior to prior art methods which rely on cumbersome analytical equipment to detect the presence of a contaminating microbe.

The term "barrier composition" or "barrier film" is used throughout the specification to describe a hydrophobic polymeric composition which is used to line a food container or packaging material and prevent water, water vapor or gas from escaping from the package. The barrier composition or film is useful for lining a can or other packaging material to produce a laminate with the hydrophilic resin containing indicator comprising a first layer of the laminate which is exposed to liquid from a food sample to allow reaction between the gas (or reactant produced from the gas) and the indicator. In an alternative embodiment, indicator coats the barrier composition or film onto which is laminated a layer of hydrophilic polymer. In this embodiment, indicator may be coated onto the surface of the hydrophobic composition in a manner such that when food liquid permeates the hydrophilic composition which coats both the indicator and the barrier composition, the indicator will react with dissolved gas or reactant and produce a colormetric reaction which may appear in a pattern on the surface of the barrier composition or film.

Barrier compositions or films which may be used in this aspect of the present invention include, for example, poly (vinylidene fluoride), poly(vinylidene chloride), rigid polyvinylchloride, nylon 6,10, phenoxy resin, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly (oxycarbonyloxy-1,4-[1,4-phenyleneisopropylidene-1,4-phenylene) (Lexan), acrylonitrile styrene copolymers (Lopac, Monsanto), acrylonitrile/methyl acrylate/butadiene copolymers (Barex, Sohio), acrylonitrile/styrene/butadiene copolymers (Cyclopac, Borg-Warner) and mixtures, thereof, among others including for example, poly-1-vinylnaphthalene, polyvinylphenyl ketone, poly-p-xylylenedodecanedioate, poly-tetramethylene-4-octenediamide, poly-tetramethylene terephthalate, poly-trimethylene-3,3'-dibenzoate, poly-terephthallic anhydride, poly-4-methyl-diamine, polyviinylene carbonate, polyvinylene laurate, polyisoprpenyl acetate, polyallylbenzene, polyvinylbutyl ether, polyvinyl formate, polyvinyl phenyl ether and polynorbornadine, among others.

The polymeric composition may line a food package, e.g., a steel can, in a manner to form a "tight coating", i.e., a coating which is designed to preclude any part of the stored food from coming into contact with the underlying can. The polymeric composition may be chosen so as to allow gases dissolved in food or other liquid to pass through and come into contact with an indicator which has been polymerized or dispersed throughout the polymeric composition. Alternatively, the indicator may be coated onto the polymeric composition and used directly or coated onto the underlying polymeric composition in combination with or underneath hydrophilic polymer which holds the indicator in place for analysis.

One of ordinary skill in the art, simply relying on readily available information regarding the permeability data for water in various hydrophilic polymeric compositions and the dissolution data of individual gases such as carbon dioxide, carbon monoxide, hydrogen sulfide, sulfur dioxide, hydrogen and ammonia which would be dissolved in the food liquid may readily determine the appropriate polymeric composition to use in a particular manner with a particular foodstuff. Thus, one of ordinary skill in the art may choose the appropriate polymeric composition to line the food container, the type and effective amount of an appropriate indicator which may be used for the gas or reactive product produced by the gas in the food liquid and based upon the food to be stored as well as a microorganism or bacteria to be detected. For example, in the case of detecting *E. coli* contamination in cans, one of ordinary skill in the art will recognize that it is appropriate to choose polymers containing an indicator which detects trace quantities of carbon dioxide (in the form of carbonate) produced by the bacteria. In the case of other bacteria and foodstuffs, the polymeric composition will be modified to accommodate the appropriate indicator and food, based upon the gas or reactive species which is produced by the gas given off by the microbe.

The term "gas" is used to describe gaseous products of metabolism or growth of contaminating bacteria in food which is stored in the storage cans according to the present invention. Exemplary gases which are detected in the present invention include carbon dioxide, carbon monoxide, hydrogen sulfide, sulfur dioxide, hydrogen and ammonia, among others.

The term "permeable" is used to describe polymeric compositions according to the present invention which allow sufficient quantities of water and gasses (preferably, which are dissolved in the food liquid) to flow through the composition and interact or react with the indicator.

The term "package" is used to describe any container, can, pail, bottle, bottle cap or stopper, drum, packing material or wrap (especially including transparent wrap) in which food may be stored. In the present invention the food package is lined with a polymeric composition which contains or is coated by an indicator. The indicator, where it is coated onto a composition may be further coated with an additional polymeric composition, preferably permeable to the water within which a gas or gases to be detected is dissolved.

The term "contaminating bacteria" is used to describe microorganisms such as bacteria which, if present in food, create a potential health hazard for the consumer. Life-threatening sickness, even death, may result from the consumption of food contaminated with any number of deleterious microorganisms such as bacteria. Although numerous contaminating microoraganisms including bacteria may be detected using the present invention, the most common bacteria which create health problems in food include Salmonella sp., Streptococcus sp., Shigella sp., Botulism sp., *Escherichia coli* and other Coliform bacteria. In the case of *Escherichia coli,* a number of types may be problematic, but are detected by the present invention including, for example, enterotoxigenic (ETEC), enteroinvasive (EIEC), enterohemorrhagic (EHEC), enteropathogenic (EPEC) and enteradherent (EAEC), among others. Numerous *E. coli* of 0-serogroups may be problematic including for example, (EPEC) 026:K60, 055:K59, 0111:L58, 0127:K63, 086:K61, 0119:K69, 0124:K72, 0125:K70, 0126:K71, 0128:K67, 018:K77, 020:K61, 020:K84, 028:K73, 044:K74, 0112:K66; (ETEC) 06, 08, 011, 078; (EIEC) 028:K73, 0112:K66, 0124:K72, 0143:$K^b$, 0144:$K^c$; and (EHEC) 0157:H7, among others. A particularly onerous serogroup of *E. coli* is (EHEC) 0157:H7.

The above-referenced bacteria, among others, as a consequence of growth and/or metabolism, produce significant quantities of gasses including carbon dioxide, carbon monoxide, hydrogen sulfide, sulfur dioxide or ammonia gas, among others. The gases produced by these deleterious microorganisms may be readily detected using the present invention, thus alerting the consumer to the potential dangers of consuming contaminated food.

The bacteria generally remain dormant as spores in the food product until certain conditions exist. The most prevalent, condition is a constant exposure to ambient temperatures of about 45.5° C.±2° C. outside the can, which promotes growth and germination of the bacterial spore, although other conditions may precipitate growth and germination. As the bacterial spore grows it releases an effervescent gas, which dissolves in the food liquid, migrates toward the indicator as a consequence of the permeablility of the hydrophilic polymer and produces a chemical reaction with the indicator, either directly by the dissolved gas or alternatively, through a reactive intermediate which is produced by the gas and water.

The term "indicator" is used to describe chemical compounds which may be added to or coated onto polymeric compositions according to the present invention in amounts effective to detect gases which are produced by contaminating bacteria in food. Indicators are chemical compounds which undergo a chemical reaction in the presence of a gas or an acid or base conjugate of a gas and produce a calorimetric species in response to the acid or base produced. The chemical response of the indicator is generally concentration dependent. Indicators for use in the present invention may be solids or liquids. In the present invention, gases which are produced by contaminating bacteria including carbon dioxide, sulfur dioxide and ammonia gas, among others, react with the chosen indicator which has been polymerized or dispersed throughout the polymeric composition. The indicator produces a calorimetric reaction upon exposure to the gas or an acid or base conjugate of the gas, thus evidencing the presence of contaminating bacteria in the analyzed food sample. In certain preferred versions of the present invention, the indicator will produce an irreversible calorimetric reaction upon exposure to the gas produced by the contaminating bacteria, thus minimizing the possibility that leakage of the gas from the food storage container will result in a failure to detect contamination.

Exemplary indicators for the detection of carbon dioxide, hydrogen sulfide or sulfur dioxide include, for example, xylenol blue (p-Xylenolsulfonephthalein), bromocresol purple (5', 5"-Dibromo-o-cresolsulfonephthalein), bromocresol green (Tetrabromo-m-cresolsulfonephthalein), Congo red, cresol red (o-Cresolsulfonephthalein), phenolphthalein, bromothymol blue (3',3"-Dibromothymolsulfonephthalein), p-naphtholbenzein (4-[alpha-(4-Hydroxy-1-naphthyl) benzylidene]-1(4H)-naphthalenone) and neutral red (3-Amino-7-dimethylamino-2-methylphenazine Chloride), among others. These indicators all provide calorimetric responses to the addition of quanities of acid, in the form of carbonic acid or sulfuric acid (from $CO_2$ or $H_2SO_4$ production by contaminating bacteria). An exemplary indicator for the detection of ammonia produced by contaminating bacteria comprises a mixture of potassium iodide, mercuric (III) iodide, sodium borate, sodium hydroxide and water (in the ratio of 1.5:2.5:2.5:3.5:90 parts by weight). Other indicators for use in the present invention include, for example, neutral red (3-amino-7-dimethylamino-8-methylphenazine chloride, nile blue, (5-amino-9-diethylaminobenzo[a]-phenazoxonium chloride, thymolphthalein, crystal violet (Hexamethyl-p-rosaniline chloride), hydroxy naphthol blue [disodium salt of 1-(2-naptholazo-3,6-disulfonic acid)-2-napththol-4-sulfonic acid], malachite green oxalate and methyl orange (helianthin or tropzolin D— the sodium salt of dimethyl aminoazobenzene sulfonic acid or dimethylaminoazobenzene sodium sulfonate), alizarin, crystal violet, methyl red, phenol red, among others, including mixtures of these indicators.

Indicators which are advantageouusly employed in the present invention may be dispersed or polymerized throughout the polymeric composition or alternatively, simply coated onto the polymeric composition (lining of the food package). In the case of indicators which are polymerized throughout the polymeric composition, the indicators may be modified and placed in monomeric form in order to participate in the polymerization reaction and become part of a backbone or sidechain of the polymeric composition.

The amount of indicator used in the present invention, i.e., the amount of indicator which is either dispersed or polymerized throughout the hydrophilic polymeric composition generally falls within the range of about 1 part per billion ($10^{-9}$, about $1\times10^{-7}\%$ by weight) to about 5 parts per hundred (5% by weight), preferably about 1 part per million ($10^{-6}$, about $1\times10^{-4}\%$ by weight) to about 1 part per hundred (1% by weight), more preferably about 1 part per 10,000 (0.001%) to about 1 part in 500 (about 0.5% by weight) and more preferably about 1 part in 1,000 (about 0.1%) to about 1 part in 500 (about 0.5% by weight) based upon the sensitivity of the indicator, the amount of gas produced by a microbe, the concentration of gas in the food liquid to be analyzed, the amount of polymeric composition utilized and the extent the polymeric composition is permeable to water. One of ordinary skill readily will be able to determine the type and amount of indicator to be included in polymeric compositions according to the present invention. In certain aspects of the present invention, when the indicator is simply coated on a can lining or hydrophobic polymer, the indicator is concentrated within a particular area on the coating or polymer and the amount of indicator will be somewhat concentrated. The amount used in this instance is that amount, which, when reacted with a gas or reactant produced by gas and food liquid, will produce a calorimetric reaction which is readily visible to the naked eye. Combinations of indicators to detect more than one gas are clearly contemplated by the present invention.

The present invention may be used in standard food cans or alternatively, may be used in other packing materials, such as plastic bags (especially in the case of sea food), saran wrap or cellophane or moisture barrier packing (in the case of storing meats, cheese, poultry, etc.).

Exemplary uses of the present invention include the following, among others:

disposable inserts for the lids of plastic food containers;

covers for frozen and canned fish including commercial fish containers such as oyster containers;

food wrap for food leftovers, backpack food, other types of food;

cooking bags for fowl, e.g. turkey, chicken, pheasant, doves, etc.;

plastic household shelf liners;

inside jar covers, e.g., peanut butter, ice cream, jellies; jams, other food products;

rolls of "tear-off" plastic sheets, bags for household uses;

frozen food bags and other plastic food storage containers;

cutting board covers;

package material for drugs and cosmetics;

food wrap for meat, beef, steaks, fish, fruits or vegetables;

linings, lids or top inserts for refrigerator bins (disposable).

In another aspect, the present invention may be a warning system for the presence of certain contaminants within containers; of processed or non-processed comestibles. A positive analysis will alert a consumer to avoid eating contaminated food.

The uniqueness of this invention is manifest in the following exemplary manner:

1) The capability of ascertaining the presence or absence of contaminants within a container while the contents are in a closed and sealed atmosphere by way of an on-going, and continuous analysis procedure.

2) The container is prepared for the continuing analysis procedure during the manufacturing process where the polymeric composition containing indicator may be applied, directly onto the package or over a standard package (can) coating with a clear USDA or FDA approved indicator solution suspended or dispersed in the polymeric composition and applied by various methods to the package, e.g., sprayed, roller coated, printed, stamped, etc. The polymeric composition containing the indicator will dry, polymerize, convert or cross-link at the specification of the container fill line.

During the container manufacture procedure, the indicator solution, being clear when applied, may be printed or otherwise applied, over standard internal can coatings so as to convey a message to whomever opens the container. Exemplary messages may read:

WARNING! DO NOT EAT THE CONTENTS OF THIS CAN, or

WARNING! BEFORE EATING, THE CONTENTS OF THIS CAN MUST BE HEATED TO 150° F. FOR FIVE MINUTES, or

WARNING! DO NOT EAT, RETURN TO STORE FOR REFUND.

When applied, the indicator remains clear or maintains a particular color which evidences that no reaction or contamination has occurred. When the food package is filled, closed and sealed, the continuing chemical analysis begins. If the food package contains contaminated toxic organic materials, these will begin to grow and multiply within the closed and sealed atmosphere, producing any one or more of carbon dioxide, sulfur dioxide or ammonia, among others during metabolic processes.

The microrganism growth particles may be spores or bacteria which produce gas as they grow and multiply. As the gas accumulates, it migrates in an upward direction to accumulate in a top end area. As the gas contacts the indicator, the indicator ink and gas react, thus causing the indicator to change from a clear or original color to a predetermined color, thus making the warning legible. If no gas is produced, there will be no reaction.

This invention may also be employed in additional applications. Employing the polymeric composition containing an indicator on the inside of a container, i.e., a can, jar lid, bottle cap, 5 gallon pail cover or 55 gallon drum lid, among other packages, the indicator or polymeric composition containing indicator may be deposited on either or both sides of "plastic wrap" sheets or rolls. With both sides of the plastic material printed, when used as a wrapper for table ready comestibles, the user applying the wrap to the food product will not be confused as to which side of the plastic wrap has been printed because the indicator is applied to both sides of the plastic wrap.

As in the instance of comestibles packaged in cans for sale to the general public or for temporary storage in large open containers in processing plants or retail markets, the organisms generate gases as they grow and multiply. The gases will migrate to the indicator within the polymeric composition or which coats a lining or hydrophobic composition and produce a calorimetric reaction, thus, preferably causing a warning to appear.

The following examples are provided to illustrate the present invention and should not be misunderstood to limit the scope of the present invention in any way.

EXAMPLES

Testing of Indicator in a PVA/PVC Polymer Mixture

This example illustrates the use of the present invention in a manner consistent with the analysis of microbial contamination in food sources. Using 100 grams each of PVA and PVC, a sample of phenolphthalein (about 0.1–0.2% by weight of the PVA and PVC) was added to an aqueuous solution of PVA and PVC in a 200 ml glass cup and mixed on a laboratory high speed disperser until the indicator dissolved thoroughly in the dissolved polymers. This produced a PVA/PVC/indicator mixture which was used for further testing.

An aqueous PVA/PVC mixture (no indicator) was prepared and applied onto an aluminum laboratory test panel available from the Morrist Company (among a number of other possible suppliers) and drawn down over the test panel to produce a first polymer layer. When this PVA/PVC coating on the test panel was completely dried, a drop of the aqueous PVA/PVC/indicator mixture was placed onto the first PVA/PVC coating and drawn down to produce a film.

After the PVA/PVC/indicator mixture was dry, the aluminum panel was placed into a gas chamber containing a water tower which was outfitted to deliver a gas in water vapor (choice of gas may be made at the gas manifold), which may be $CO_2$, ammonia or other gas to be tested. The water vapor containing the dissolved gas is delivered to the surface of the aluminum test panel prepared above. Essentially, the gas is bubbled through the water tower and the resulting water vapor which emerges from the water tower contains the gas of choice dissolved in the vapor (as well as oxygen, nitrogen and other inert atmospheric gasses). The water vapor fills the gas chamber and is continuously evacuated with a vacuum. The use of $CO_2$ in water vapor may be used to produce a pH within the range of 5–6 within the water vapor, which produces a color change from clear to pink on the aluminum panel. As the pH is adjusted by utilizing ammonia in water vapor to produce a pH of about 9–9.5, the color change is a vivid red. The color change is irreversible.

Standard Can

The following is a description of the manufacturing process of a standard can that can be used in the packaging of vegetables such as corn, various kinds of beans, fruit, fruit sald, puddings, etc.

The raw material generally is a mild steel in large rolls delivered to the manufacturing site. A large roll is fed into the "slitter." The roll is then "slit" (cut), then rerolled in to various rolls, the width of which is equal to the exact height of the can in its finished state. A roll of the desired width is then painted with a vinyl paint (polyvinyl acetate or polyvinylchloride), the formula of which is compatible with the food product which is to be packaged in the finished can.

The roll is thereafter straightened and cut. The pieces are the exact size of the finsished can body. The pieces are stacked and portions of the stacks are introduced into a feeding device which is a gravity feeder inserting one body piece a time into a machine which forms the flat piece (blank) into a cylinder and passes the now cyclical "body" past an electrical resistance welder, joining the two edges together with an electrical resistance weld. The welded section is then coated with a "side seam enamel" which can tolerate the very high temperature of the welding process.

The welded cyclinder (body) moves along with the conveyer at the speed of of 400–600 can bodies per minute. The conveyor by design changes the direction of the "lie" of the can body. To this point, the can bodies have been in a horizontal position, following each other along the conveyor. They are now turned in a manner to create a side by side relationship, and then fed into a large platen with wide holes. The platen is turning in the same direction as the conveyor. As the platen turns, it takes the cans out of the conveyor line, the inside of the can is sprayed with a vinyl coating, and then the can is returned to the conveyor, the can body now moves along the conveyor a short distance. The solvent formula of the coating is adjusted to the speed of the conveyor and the distance traveled to the oven.

The body is then made. There are generally two and three piece can assemblies. Various formulas are used in the internal finish of the cans. Some have 100% solids and need no "flash off time." Other coatings may employ thermal conversion, chemical reactions or ultra violet light to ensure complete polymerization.

A two piece can involves a body made by deep draw. This method of manufacture would have a single piece deep drawn in the center of the flat stock resulting in a body with the bottom intact in a single impact referred to as a "deep draw." This can be accomplished singularly or by a multiple impact changing tools as the draw is deepened to a desired depth or height of the can. Three piece cans, the most widely-used design, involves a body, a bottom and a top.

The top and bottom of the can are both refrred to as lids, and are made from a single sheet of steel which is die cut to obtain a maximum number of lids per piece of sheet stock. Tops and bottoms are separated from the flash and they are printed with the indicator directly or along with the polymeric composition containing the indicator on the inside portion of the lids. The indicator applied will be specific for the product canned or may be formulated to be sensitive to several contaminating microorganisms.

The indicator used for a particular canning run must be compatible with the internal can coating and maintain acceptable adhesion whether the product is going to be frozen or cooked at a high temperature. Because the food product inside the can comes in contact with the food, the indicator is classified as a food additive and must meet all standards, as set forth by the FDA for food additives.

In the case of a three part can, there is a bottom, a body and a top. The bottom is attached in one of several methods to the body. The cans are filled with food product and the lid is fastened using an approved method. Some cans containing certain food products may be further processed (cooked) at this point. Other cans have fully processed food filled at the start. The filled can is now ready for labeling, packing and shipping.

During storage, if contaminant bacteria are present in the stored food, the gas produced by the bacteria will produce a reaction in the indicator in the lid (top or bottom) of the can. A color reaction will indicate the presence of deleterious quantities of bacteria, no reaction indicates the food product is safe for consumption.

Food Wrap

Generally, two types of vinyl compounds are used in food wrap, e.g., polyvinyl acetate and polyvinyl chloride. The treatment of either of these vinyl solutions is the same. The indicator, dispersed in a compatible carrier, is blended into the vinyl wrap mixture while the ingredients are in a liquid state. Both solutions together will be further processed until the liquid vinyl compound is processed into sheets, then into rolls.

When the wrap is used to cover food products and contaminant bacteria, if present, commence to grow and generate gases. When the gases reach the food wrap and contact the indicator bearing cover, the indicator will react by changing color. The absence of toxin is evidenced by no reaction.

It is to be understood that the embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

What is claimed is:

1. A method for detecting the presence or absence of contaminating bacteria in a stored food sample comprising storing food in a package having as a lining a hydrophilic polymeric composition said composition being permeable to water or water vapor and at least one gas dissolved in said water or water vapor released by said bacteria selected from the group consisting of carbon dioxide, hydrogen sulfide, sulfur dioxide and ammonia gas to allow the formation of carbonic acid, sulfuric acid, hydrogen sulfide and ammonium hydroxide and containing an amount of an indicator effective for visibly detecting the presence or abscence of said carbonic acid, sulfuric acid, hydrogen sulfide or ammonium hydroxide; said indicator being polymerized or dispersed throughout said polymeric composition.

2. The method according to claim 1 wherein said hydrophilic polymeric composition selected from the group consisting of selected from the group consisting of poly) hydroxyethyl methacrylate, (poly)hydroxypropyl methacrylate, (poly)glycerol methacrylate, copolymers of hydroxyethyl methacrylate, hydroxypropyl methacrylate or glycerol methacrylate and methacrylic acid, aminoacrylate and aminomethacrylate, (poly)vinyl pyrrolidone, (poly) vinylpyridine, polar polyamides, methyl cellulose, hydroxypropyl cellulose, hydroxyethyl cellulose, hydroxypropyl methylcellulose, ethyl hydroxyethylcellulose, carboxymethyl cellulose, cellulose acetate, cellulose acetate butyrate, cellulose acetate propionate, cellulose nitrate, polyvinyl acetate, polyvinyl alcohol, copolymers of polyvinyl acetate and polyvinyl alcohol, hydroxylmodified copolymers of vinyl acetate and vinylchloride, polyesters and polyurethanes containing at least about 10% by weight of polyethylene oxide, styrene/methacrylic acid/hydroxyethyl methacrylate copolymers, styrene/methacrylic acid/ hydroxypropyl methacrylate copolymers, methylmethacrylate/methacrylic acid copolymers, ethyl methacrylate/styrene/methacrylic acid copolymers, ethyl methacrylate/methyl methacrylate/ styrene/methacrylic acid copolymers, polytetrafluoroethylene and hydrophilic cellulose copolymers.

3. A method for detecting the presence or absence of contaminating bacteria in a stored food sample comprising storing food in a package having as a lining a hydrophobic polymeric composition, said hydrophobic composition being coated with a hydrophilic polymeric composition, said hydrophilic composition being permeable to water or water vapor and at least one gas dissolved in said water or water vapor released by said bacteria selected from the group consisting of carbon dioxide, hydrogen sulfide, sulfur dioxide and ammonia gas to allow the formation of carbonic acid, sulfuric acid, acid, ammonium hydroxide and containing an amount of an indicator effective for visibly detecting the presence or abscence of said carbonic acid, sulfuric acid, hydrogen sulfide or,ammonium hydroxide; said indicator being polymerized or dispersed throughout said hydrophilic polymeric composition.

4. The method according to claim 3 wherein said hydrophilic polymeric composition is selected from the group consisting of selected from the group consisting of poly) hydroxyethyl methacrylate, (poly)hydroxypropyl methacrylate, (poly)glycerol methacrylate, copolymers of hydroxyethyl methacrylate, hydroxypropyl methacrylate or glycerol methacrylate and methacrylic acid, aminoacrylate and aminomethacrylate, (poly)vinyl pyrrolidone, (poly) vinylpyridine, polar polyamides, methyl cellulose, hydroxypropyl cellulose, hydroxyethyl cellulose, hydroxypropyl methylcellulose, ethyl hydroxyethylcellulose, carboxymethyl cellulose, cellulose acetate, cellulose acetate butyrate, cellulose acetate propionate, cellulose nitrate, polyvinyl acetate, polyvinyl alcohol, copolymers of polyvinyl acetate and polyvinyl alcohol, hydroxylmodified copolymers of vinyl acetate and vinylchloride, polyesters and polyurethanes containing at least about 10% by weight of polyethylene oxide, styrene/methacrylic acid/hydroxyethyl methacrylate copolymers, styrene/methacrylic acid/ hydroxypropyl methacrylate copolymers, methylmethacrylate/methacrylic acid copolymers, ethyl methacrylate/styrene/methacrylic acid copolymers, ethyl methacrylate/methyl methacrylate/ styrene/methacrylic acid copolymers, polytetrafluoroethylene and hydrophilic cellulose copolymers.

5. A food storage package adapted to detect gas released by bacteria which may contaminate food stored in said package, said package being lined with a hydrophilic polymeric composition, said hydrophilic composition being permeable to water or water vapor and at least one gas dissolved in said water or water vapor released by said bacteria selected from the group consisting of carbon dioxide, hydrogen sulfide, sulfur dioxide and ammonia gas to allow the formation of carbonic acid, sulfuric acid, sulfur and ammonium hydroxide and containing an amount of an indicator effective for visibly detecting the presence or abscence of said carbonic acid, sulfuric acid, hydrogen sulfide or ammonium hydroxide; said indicator being polymerized or dispersed throughout said hydrophilic polymeric composition.

6. The package according to claim 5 wherein said hydrophilic composition is selected from the group consisting of poly)hydroxyethyl methacrylate, (poly)hydroxypropyl methacrylate, (poly)glycerol methacrylate, copolymers of hydroxyethyl methacrylate, hydroxypropyl methacrylate or glycerol methacrylate and methacrylic acid, aminoacrylate and aminomethacrylate, (poly)vinyl pyrrolidone, (poly) vinylpyridine, polar polyamides, methyl cellulose, hydroxypropyl cellulose, hydroxyethyl cellulose, hydroxypropyl methylcellulose, ethyl hydroxyethylcellulose, carboxymethyl cellulose, cellulose acetate, cellulose acetate butyrate, cellulose acetate propionate, cellulose nitrate, polyvinyl acetate, polyvinyl alcohol, copolymers of polyvinyl acetate and polyvinyl alcohol, hydroxylmodified copolymers of vinyl acetate and vinylchloride, polyesters and polyurethanes containing at least about 10% by weight of polyethylene oxide, styrene/methacrylic acid/hydroxyethyl methacrylate copolymers, styrene/methacrylic acid/ hydroxypropyl methacrylate copolymers, methylmethacrylate/methacrylic acid copolymers, ethyl methacrylate/styrene/methacrylic acid copolymers, ethyl methacrylate/methyl methacrylate/ styrene/methacrylic acid copolymers, polytetrafluoroethylene and hydrophilic cellulose copolymers.

7. The method according to claim 1 wherein said bacteria is selected from the group consisting of Salmonella sp., Streptococcus sp., Shigella sp., Botulism sp., *Escherichia coli* and *Coliform bacteria*.

8. The method according to claim 7 wherein said bacteria is *E. coli* serogroup 0157:H7.

9. The method according to claim 1 wherein said indicator is selected from the group consisting of xylenol blue, bromocresol purple, bromocresol green, Congo red, cresol red, phenolphthalein, bromothymol blue, p-naphtholbenzein, neutral red, a mixture of potassium iodide, mercuric (III) iodide, sodium borate, sodium hydroxide and water, nile blue, thymolphthalein, crystal violet, hydroxy naphthol blue, malachite green oxalate, methyl orange, alizarin, crystal violet, methyl red, phenol red and mixtures, thereof.

10. The method according to claim 2 wherein said indicator is selected from the group consisting of xylenol blue, bromocresol purple, bromocresol green, cresol red, phenolphthalein, bromothymol blue, p-naphtholbenzein and neutral red.

11. The method according to claim 1 wherein said indicator is a mixture of potassium iodide, mercuric (III) iodide, sodium borate, sodium hydroxide and water.

12. The method according to claim 3 wherein said hydrophobic polymeric composition is selected from the group consisting of poly(vinylidene fluoride), poly(vinylidene chloride), phenoxy resin, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4-[1,4-phenyleneisopropylidene -1,4-phenylene), acrylonitrile styrene copolymers, acrylonitrile/methyl acrylate/butadiene copolymers, acrylonitrile/styrene/butadiene copolymers, poly-1-vinylnaphthalene, polyvinylphenyl ketone, poly-p-xylylenedodecanedioate, poly-tetramethylene-4-octenediamide, poly-tetramethylene terephthalate, poly-trimethylene-3,3'-dibenzoate, poly-terephthallic anhydride, poly-4-methyl-diamine, polyvinylene carbonate, polyvinylene laurate, polyisoprpenyl acetate, polyallylbenzene, polyvinylbutyl ether, polyvinyl formate, polyvinyl phenyl ether, polynorbornadine, polycarbonate, hydrophobic polyesters and polyurethanes, and mixtures, thereof.

13. The method according to claim 3 wherein said bacteria is selected from the group consisting of Salmonella sp., Streptococcus sp., Shigella sp., Botulism sp., *Escherichia coli* and Coliform bacteria.

14. The method according to claim 3 wherein said indicator is selected from the group consisting of xylenol blue, bromocresol purple, bromocresol green, Congo red, cresol red, phenolphthalein, bromothymol blue, p-naphtholbenzein, neutral red, a mixture of potassium iodide, mercuric (III) iodide, sodium borate, sodium hydroxide and water, nile blue, thymolphthalein, crystal violet, hydroxy naphthol blue, malachite green oxalate, methyl orange, alizarin, crystal violet, methyl red, phenol red and mixtures, thereof.

15. The method according to claim 3 wherein said indicator is selected from the group consisting of xylenol blue, bromocresol purple, bromocresol green, Congo red, cresol red, phenolphthalein, bromothymol blue, p-naphtholbenzein, neutral red, a mixture of potassium iodide, mercuric (III) iodide, sodium borate, sodium hydroxide and water, nile blue, thymolphthalein, crystal violet, hydroxy naphthol blue, malachite green oxalate, methyl orange, alizarin, crystal violet, methyl red, phenol red and mixtures, thereof.

16. The method according to claim 15 wherein said indicator is selected from the group consisting of xylenol blue, bromocresol purple, bromocresol green, cresol red, phenolphthalein, bromothymol blue, p-naphtholbenzein and neutral red.

17. The food storage package according to claim 5 wherein said bacteria is selected from the group consisting of Salmonella sp., Streptococcus sp., Shigella sp., Botulism sp., *Escherichia coli* and Coliform bacteria.

18. The food storage package according to claim 17 wherein said bacteria is *E. coli*.

19. The food storage package according to claim 5 wherein said indicator is selected from the group consisting of xylenol blue, bromocresol purple, bromocresol green, Congo red, cresol red, phenolphthalein, bromothymol blue, p-naphtholbenzein, neutral red, a mixture of potassium iodide, mercuric (III) iodide, sodium borate, sodium hydroxide and water, nile blue, thymolphthalein, crystal violet, hydroxy naphthol blue, malachite green oxalate, methyl orange, alizarin, crystal violet, methyl red, phenol red and mixtures, thereof.

20. The food storage package according to claim 17 wherein said hydrophilic polymeric composition coats a hydrophobic polymeric composition onto which said indicator is coated, said hydrophobic polymeric composition being selected from the group consisting of poly(vinylidene fluoride), poly(vinylidene chloride), phenoxy resin, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4-[1,4-phenyleneisopropylidene-1,4-phenylene), acrylonitrile styrene copolymers, acrylonitrile/methyl acrylate/butadiene copolymers, acrylonitrile/styrene/butadiene copolymers, poly-1-vinylnaphthalene, polyvinylphenyl ketone, poly-p-xylylenedodecanedioate, poly-tetramethylene-4-octenediamide, poly-tetramethylene terephthalate, poly-trimethylene-3,3'-dibenzoate, poly-terephthallic anhydride, poly-4-methyl-diamine, polyvinylene carbonate, polyvinylene laurate, polyisoprpenyl acetate, polyallylbenzene, polyvinylbutyl ether, polyvinyl formate, polyvinyl phenyl ether, polynorbornadine, polycarbonate, hydrophobic polyesters and polyurethanes, and mixtures, thereof.

\* \* \* \* \*